United States Patent
Ward et al.

(10) Patent No.: US 10,780,222 B2
(45) Date of Patent: Sep. 22, 2020

(54) MEASUREMENT OF GLUCOSE IN AN INSULIN DELIVERY CATHETER BY MINIMIZING THE ADVERSE EFFECTS OF INSULIN PRESERVATIVES

(71) Applicant: Pacific Diabetes Technologies Inc, Portland, OR (US)

(72) Inventors: William Kenneth Ward, Portland, OR (US); Robert S Cargill, Portland, OR (US); Gabriel Heinrich, Portland, OR (US); Sheila Benware, Clackamas, OR (US); Mark Vreeke, Aliso Viejo, CA (US); Joseph D. Kowalski, Portland, OR (US); Thomas Seidl, Tigard, OR (US)

(73) Assignee: PACIFIC DIABETES TECHNOLOGIES INC, Portland, OR (US)

( * ) Notice: Subject to any disclaimer, the term of this patent is extended or adjusted under 35 U.S.C. 154(b) by 513 days.

(21) Appl. No.: 15/169,432

(22) Filed: May 31, 2016

(65) Prior Publication Data

US 2016/0354542 A1 Dec. 8, 2016

Related U.S. Application Data

(60) Provisional application No. 62/170,655, filed on Jun. 3, 2015.

(51) Int. Cl.
*A61B 5/00* (2006.01)
*A61M 5/172* (2006.01)
(Continued)

(52) U.S. Cl.
CPC ......... *A61M 5/1723* (2013.01); *A61B 5/1473* (2013.01); *A61B 5/14503* (2013.01);
(Continued)

(58) Field of Classification Search
None
See application file for complete search history.

(56) References Cited

U.S. PATENT DOCUMENTS

| 5,165,407 A | 11/1992 | Wilson |
| 5,174,291 A | 12/1992 | Schoonen |

(Continued)

FOREIGN PATENT DOCUMENTS

| CA | 2347378 | 4/2000 |
| EP | 1327881 | 7/2003 |

(Continued)

OTHER PUBLICATIONS

D. Peel, Reminder: cresol and phenol preservatives interfere with analysis for glucose with the YSI Analyzer; Aug. 1983, Clinical Chemistry, vol. 29 Issue 8, pp. 1558-1559 (Year: 1983).*

(Continued)

*Primary Examiner* — Christian Jang
*Assistant Examiner* — Sarah R Kingsley
(74) *Attorney, Agent, or Firm* — Wilson Sonsini Goodrich & Rosati

(57) ABSTRACT

This disclosure teaches the concept, and method of creating, a dual use device intended for persons who take insulin. In one embodiment, the novel device is an insulin delivery cannula, the outer wall of which contains electrodes, chemical compounds and electrical interconnects that allow continuous glucose sensing and delivery of data to a remote device. Heretofore, the main problem in attempting to sense glucose at the site of insulin delivery has been the high current resulting from oxidation by the sensor of the preservatives in the insulin formulations. One means of eliminating these interferences is to poise the indicating electrode(s) of the sensor at a bias sufficiently low to avoid the signal from oxidation of the preservatives. One way of (Continued)

obtaining a glucose signal at a low bias is to use an osmium-ligand-polymer complex instead of conventional hydrogen peroxide sensing. Another is to use a size exclusion filter located in line with the insulin delivery tubing in order to remove the smaller phenolic preservative molecules while allowing the larger insulin molecules to pass unimpeded. These filtration concepts can also be more broadly applied, that is, the general concept of removal of unwanted drug formulation excipients from a drug delivery system.

11 Claims, 10 Drawing Sheets

(51) Int. Cl.
    *A61B 5/145*     (2006.01)
    *A61B 5/1473*     (2006.01)
    *A61M 5/158*     (2006.01)
    *A61M 5/165*     (2006.01)
    *A61M 5/142*     (2006.01)

(52) U.S. Cl.
    CPC ......... *A61B 5/14532* (2013.01); *A61M 5/142* (2013.01); *A61M 5/158* (2013.01); *A61M 5/165* (2013.01); *A61M 2005/1587* (2013.01); *A61M 2230/005* (2013.01); *A61M 2230/201* (2013.01)

(56) References Cited

U.S. PATENT DOCUMENTS

| | | | |
|---|---|---|---|
| 5,176,632 A | 1/1993 | Bernardi | |
| 5,431,160 A | 7/1995 | Wilkins | |
| 5,476,776 A | 12/1995 | Wilkins | |
| 5,868,711 A * | 2/1999 | Kramer | A61B 17/3472 604/136 |
| 5,936,061 A | 8/1999 | Andersson et al. | |
| 6,210,326 B1 | 4/2001 | Ehwarld | |
| 6,605,048 B1 | 8/2003 | Levin | |
| 6,613,205 B1 | 9/2003 | Steiner | |
| 6,613,379 B2 | 9/2003 | Ward | |
| 6,695,958 B1 | 2/2004 | Adam | |
| 6,814,845 B2 | 11/2004 | Wilson | |
| 6,892,085 B2 | 5/2005 | McIvor | |
| 7,003,336 B2 | 2/2006 | Holker | |
| 7,074,307 B2 | 7/2006 | Simpson | |
| 7,120,483 B2 | 10/2006 | Russell | |
| 7,134,999 B2 | 11/2006 | Brauker | |
| 7,146,202 B2 | 12/2006 | Ward | |
| 7,228,162 B2 | 6/2007 | Ward | |
| 7,379,765 B2 | 5/2008 | Petisce | |
| 7,399,277 B2 | 7/2008 | Saidara | |
| 7,471,972 B2 | 12/2008 | Rhodes | |
| 7,499,738 B2 | 3/2009 | Gerber | |
| 7,529,574 B2 | 5/2009 | Jansen | |
| 7,534,330 B2 | 5/2009 | Yu | |
| 7,799,191 B2 | 9/2010 | Yu | |
| 7,826,879 B2 | 11/2010 | Hoss | |
| 7,896,809 B2 | 3/2011 | Simpson | |
| 7,901,354 B2 | 3/2011 | Shults | |
| 7,905,833 B2 | 3/2011 | Brister | |
| 7,949,381 B2 | 5/2011 | Brister | |
| 7,967,752 B2 | 6/2011 | Ocvirk | |
| 8,000,901 B2 | 8/2011 | Brauker | |
| 8,017,314 B2 | 9/2011 | Abel | |
| 8,060,174 B2 | 11/2011 | Simpson | |
| 8,133,178 B2 | 3/2012 | Brauker | |
| 8,155,722 B2 | 4/2012 | Feldman | |
| 8,160,669 B2 | 4/2012 | Brauker | |
| 8,170,803 B2 | 5/2012 | Kamath | |
| 8,187,433 B2 | 5/2012 | Ward | |
| 8,231,531 B2 | 7/2012 | Brister | |
| 8,268,143 B2 | 9/2012 | Liu | |
| 8,277,636 B2 | 10/2012 | Sode | |
| 8,277,713 B2 | 10/2012 | Petisce | |
| 8,326,393 B2 | 12/2012 | Kotzan | |
| 8,373,421 B2 | 2/2013 | Lindegger | |
| 8,483,791 B2 | 7/2013 | Brister | |
| 8,483,793 B2 | 7/2013 | Simpson | |
| 8,509,871 B2 | 8/2013 | Rhodes | |
| 8,515,518 B2 | 8/2013 | Ouyang | |
| 8,515,519 B2 | 8/2013 | Brister | |
| 8,527,024 B2 | 9/2013 | Staib | |
| 8,543,184 B2 | 9/2013 | Boock | |
| 8,548,551 B2 | 10/2013 | Kamath | |
| 8,571,625 B2 | 10/2013 | Kamath | |
| 8,512,276 B2 | 11/2013 | Talbot | |
| 8,577,438 B2 | 11/2013 | Kube | |
| 8,608,922 B2 | 12/2013 | Papakimitrakopoulos | |
| 8,620,398 B2 | 12/2013 | Feldman | |
| 8,679,016 B2 | 3/2014 | Mastrototaro | |
| 8,650,751 B2 | 8/2014 | Feldman | |
| 8,812,072 B2 | 8/2014 | Brister | |
| 8,886,273 B2 | 11/2014 | Li | |
| 9,131,885 B2 | 9/2015 | Simpson | |
| 2005/0118726 A1 | 6/2005 | Schultz | |
| 2006/0000710 A1 | 1/2006 | Weidenhaupt | |
| 2006/0025717 A1 | 2/2006 | Zimmerman | |
| 2006/0263839 A1 | 11/2006 | Ward et al. | |
| 2009/0062767 A1 | 3/2009 | Van Antwerp | |
| 2009/0298104 A1 * | 12/2009 | Liu | C12Q 1/006 435/14 |
| 2010/0256593 A1 * | 10/2010 | Yodfat | A61M 5/14248 604/504 |
| 2011/0021889 A1 * | 1/2011 | Hoss | A61B 5/14532 600/310 |
| 2011/0180405 A1 | 7/2011 | Chinnayelka | |
| 2012/0046533 A1 * | 2/2012 | Voskanyan | A61B 5/14532 600/347 |
| 2012/0138484 A1 * | 6/2012 | Bommakanti | C12Q 1/006 205/777.5 |
| 2013/0040404 A1 | 2/2013 | Crane | |
| 2013/0060106 A1 | 5/2013 | Aasmul | |
| 2013/0131482 A1 * | 5/2013 | Fedder | A61N 1/05 600/378 |
| 2014/0163346 A1 | 6/2014 | Pesantez | |
| 2014/0296823 A1 | 10/2014 | Ward | |
| 2014/0367246 A1 | 12/2014 | Shah | |
| 2015/0374905 A1 | 12/2015 | Yodfat | |
| 2016/0128636 A1 * | 5/2016 | Fedder | A61B 5/0478 264/496 |
| 2016/0136357 A1 | 5/2016 | Yang | |

FOREIGN PATENT DOCUMENTS

| | | |
|---|---|---|
| WO | 2000064492 | 11/2000 |
| WO | 2002039086 | 5/2002 |

OTHER PUBLICATIONS

Claudia Weber, Phenolic excipients of insulin formulations induce cell death, pro-inflammatory signaling and MCP-1 release, Dec. 2014, Toxicology Reports, 2, pp. 194-202 (Year: 2014).*
Alzoubi K., S. Lu and M. Poliks (2011). Journal Article "Experimental and Analytical Studies on the High Cycle Fatigue of Thin Film Metal on PET Substrate for Flexible Electronics Applications." IEEE Transactions on Components, Packaging, and Manufacturing Technology vol. 2.
Ohara, TJ, R. Rajagopalan, A. Heller (1994) Journal Article "Wired enzyme electrodes for amperometric determination of glucose or lactate in the presence of interfering substances" Anal Chem 66:2451-2457.
Matsui, Y, Ando N, Yoshida T, Kurotobi R, Matsushita T, Ohno K. (2011) Journal Article "Modeling high adsorption capacity and kinetics of organic macromolecules on super-powdered activated carbon". Water Res. 2011;45(4):1720-8.
Lavvafi, H., J. R. Lewandowski and J. J. Lewandowski (2014). Journal Article "Flex bending fatigue testing of wires, foils and ribbons . . . " Materials Sci and Engineering 1: 123-130.

(56) References Cited

OTHER PUBLICATIONS

Peel D, Kay JD, Taylor F: Reminder: cresol and phenol preservatives interfere with analysis for glucose with the YSI Analyzer. (1983) Clinical Chemistry, vol. 29(8): pp. 1558-1559.

* cited by examiner

FIG. 10

18 — Etchant removes exposed Ag where photoresist is absent.

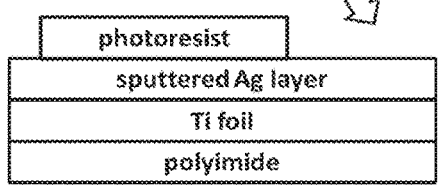

19 — Photoresist is then stripped, revealing the Ag electrode pattern.

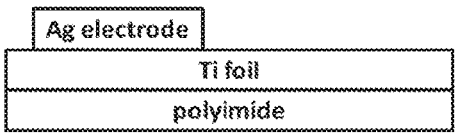

20 — Photoresist is removed where Pt is needed. Pt is then sputtered, and all photoresist is removed, which also removes Pt sputtered onto photoresist.

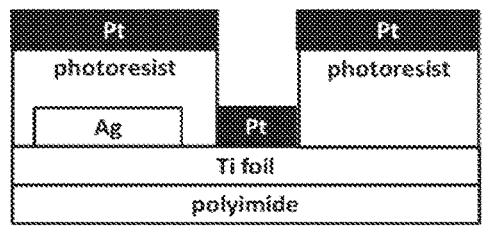

21 — Stripping the photoresist reveals the pattern for the Pt electrode.

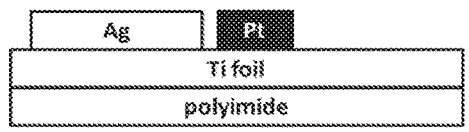

22 — Photoresist is removed wherever the Ti foil is to be removed by wet etchant, then photoresist is stripped to expose the finished electrodes.

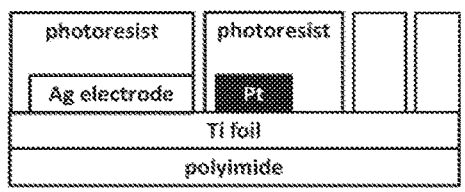

23 — Photoresist is removed, revealing the Ti pattern.

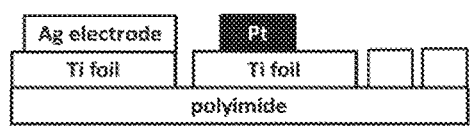

MEASUREMENT OF GLUCOSE IN AN INSULIN DELIVERY CATHETER BY MINIMIZING THE ADVERSE EFFECTS OF INSULIN PRESERVATIVES

CROSS-REFERENCE TO RELATED APPLICATION

This application claims the benefit of U.S. Provisional Application No. 62/170,655, filed Jun. 3, 2015, which is entirely incorporated herein by reference for all purposes.

BACKGROUND OF THE INVENTION

People with diabetes are at risk of developing complications such as kidney disease, eye disease, cardiovascular disease and foot/nerve disease. It is typically more difficult to control glucose levels in those who require insulin treatment as compared to those who do not. All patients with Type 1 Diabetes (T1D) require insulin and many deliver insulin by a continuous pump, which allows precise, regulated delivery of insulin 24 hours per day.

Another valuable technique in managing T1D is Continuous Glucose Monitoring (GCM), in which a subcutaneously-inserted sensor provides interstitial glucose data to the user every few minutes. Several studies, including the JDRF-sponsored trial, showed that persons of all ages who used CGM on a regular basis experienced better glycemic control than non-users, as measured by hemoglobin A1C (A1C) (*JDRF CGM Study Group. JDRF randomized clinical trial to assess the efficacy of real-time continuous glucose monitoring in the management of type* 1 *diabetes: research design and methods. Diabetes Technol Ther.* 2008; 10(4):310-21). However, this and other studies found that many patients found CGM usage cumbersome and many used CGM only sporadically. Not surprisingly, when used sporadically or rarely, CGM usage did not lead to a better glycemic control in the JDRF trial.

Daily life can be difficult for those who regularly use both an insulin pump and CGM. Such individuals must indwell two through-the-skin devices, which can increase the risk of pain, infection and other side effects compared to a single device. Persons with T1D typically carry multiple devices on the body, for example, a pump and/or syringes, a CGM receiver, a vial of insulin, a blood glucose monitor for calibrating the CGM, and blood glucose monitoring strips and lancets. The multiplicity of devices leads to a situation known as "device burden," which can lead to frustration, anger and often causes a patient to choose among devices rather than utilizing all the devices that can improve his/her health.

Because of these issues regarding device burden, there is an unmet need to integrate a CGM and insulin pump cannula into a single device.

Manufacturers' instructions state that a subcutaneous glucose sensor must be located far away from the insulin pump cannula site. In support of this statement, during pig studies, we found that current insulin formulations markedly interfere with currently-available hydrogen peroxide-measuring sensors. More specifically, we found that the preservatives in the formulations, such as phenol and m-cresol, are electroactive and interfere with CGM.

In the current invention, we teach a method in which the sensor can be successfully integrated with the insulin cannula.

DESCRIPTION OF THE RELATED ART

Rather than using a separate insulin infusion catheter and a CGM sensor, it is desirable to create a single combined device. There are many different strategies for glucose sensing that could be considered for such a combined sensing catheter. For example, there is prior art regarding the use of optical sensing technologies for glucose. US20130040404A1 to Crane et al teaches an optical glucose sensor built upon an optical waveguide. US 20050118726 A1 to Schultz et al teaches an optical sensing method based upon a glucose-binding fusion protein. US20130060106 to Aasmul et al teaches an optical fiber-based sensor having a hollow fiber filled with a glucose binding assay. WO 2000064492 A1 by Schultz and Ballerstadt et al teach a porous hollow sensor containing porous beads for the optical determination of analyte concentration. Alternative sensing strategies such as viscometry have also been disclosed (eg U.S. Pat. No. 6,210,326 B1 to Ehwarld). However, none of these is well-suited to pair CGM with drug infusion in a single device.

A common analyte sensor design is based upon the principle of amperometry, in which analytes are detected by generation of an electrochemical signal related to the analyte of interest. The sensing electrodes are commonly fabricated through the use of sputtered or evaporated thin films deposited on the surface of a substrate. Often, indicating electrodes (also known as working electrodes) are made of platinum, gold or carbon. When a positively biased indicating electrode is coupled with a reference electrode, such as silver/silver chloride, redox-active analytes can be amperometrically detected. With the addition of an enzyme layer such as glucose oxidase, a sensor can be made quite specific for the analyte glucose. The glucose oxidase is able to convert glucose, which is not readily detected amperometrically, into hydrogen peroxide which is readily detected. When thin films of metal electrodes are deposited on an appropriate polymer film such as polyimide, the resulting sensor has the added advantage of flexibility. Users might find a rigid catheter or needle uncomfortable or painful.

One problem with electrodes made from metallic thin films is fragility; the layers can delaminate when exposed to physical trauma such as impact, flexion, shear stresses, and tensile stresses. For example, Alzoubi et al found that durability of thin film electrodes is limited. More specifically, a large number of flexion cycles led to materials failure, a phenomenon known as cycle fatigue (Alzoubi K, Lu S, Sammakia B. *Experimental and Analytical Studies on the High Cycle Fatigue of Thin Film Metal on PET Substrate for Flexible Electronics Applications. IEEE Transactions, Manufacturing.* 2011; 1:43-51). While the durability of a thin film may be sufficient for short-term applications, longer term ambulatory sensing applications require a much greater ability to withstand trauma. In the case of indwelling subcutaneous sensors, the sensor must withstand repeated impacts and/or repeated flexion over a period of time lasting from 3 to 7 days or beyond. Alzoubi found that thin metal films underwent cracking which was aggravated by immersion in wet, high-salt environments such as those presented by mammalian blood or subcutaneous interstitial fluid. Consequently, the electrodes in the leading commercially-available CGM sensor (made by Dexcom, Inc) are constructed from durable solid wires rather than thin films. Examples of this design can be found in many patent disclosures. U.S. Pat. No. 8,812,072 B2 to Brister et al teaches a wire-based variable stiffness transcutaneous medical device. U.S. Pat. No. 8,543,184 B2 to Boock et al teaches a wire-based transcutaneous implantable continuous analyte sensor with a silicone-based membrane. U.S. Pat. No. 8,060,174 B2 to Simpson et al teaches a biointerface for a wire-based sensing electrode. U.S. Pat. No. 8,515,519 B2 to Brister et al teaches a transcutaneous analyte sensor assembly. U.S. Pat. No. 5,165,407 to Wilson et al teaches a flexible, solid wire-based glucose sensor. U.S. Pat. No. 7,471,972 B2 to Rhodes et al teaches a multi-electrode wire-based sensor. U.S. Pat. No. 9,131,885 B2 to Simpson et al teaches a multi-layer sensor having a solid core. However, a wire or rod has a solid core and is thus not compatible with delivery of a drug such as insulin, which requires a hollow lumen. None of these devices would be suitable for combined analyte sensing and drug delivery due to their lack of a hollow lumen.

Earlier inventions have disclosed sensors coupled with hollow catheters. In U.S. Pat. No. 8,886,273 to Li, Kamath, and Yang, the inventors teach a glucose sensor disposed within a hollow catheter. More specifically, the sensor in this invention is disposed inside a larger diameter catheter that is indwelled inside a blood vessel. Whereas such an invention is appropriate for measuring a liquid (blood) that exists within a catheter, such a design is not appropriate for a sensing catheter which is intended for measuring glucose in subcutaneous fatty tissue. For use in subcutaneous tissue, the sensing elements must be on the outer wall of the hollow catheter. Stated differently, a "wire sensor within a tube" or "tube within a tube" design will not allow proper function in subcutaneous tissue. For drug delivery, the inner lumen must be hollow. Similarly, in U.S. Pat. No. 6,695,958 B1 to Adam et al, the authors disclose a device having sensing elements located in the interior of the hollow part and designed to measure analytes in the interior lumen. For an effective subcutaneous sensing catheter, it is necessary to have an open interior (lumen) to allow for drug delivery into the body. In an embodiment of our invention, the outer wall, which is not in contact with a drug and which is bathed with glucose-containing subcutaneous interstitial fluid, is the optimal location for the sensing elements.

Other sensor configurations require the withdrawal of fluid samples from the body in order for sensing to occur. U.S. Pat. No. 5,174,291 A to Schoonen et al discloses a hollow fiber-based glucose sensor that involves dialysis with a test solution. CA 2347378 A1 to Knoll et al incorporates a hollow probe for the withdrawal of interstitial fluid. EP 1327881 A1 to Beck at al teaches a hollow electrochemical cell with internal sensing elements requiring the drawing up of the fluid sample. U.S. Pat. No. 8,277,636 B2 to Sode et al teaches a glucose dehydrogenase-based sensor incorporating an interstitial fluid sampling device. US 20060000710 A1 to Weidenhaupt et al teaches a method for determining glucose concentration that requires the use of a device that has an external sensor coupled with a fluid-sampling pump. US 20110180405 A1 to Chinnayelka teaches a sensor incorporating a hollow member and a lancet for the sampling of interstitial fluid. U.S. Pat. No. 5,176,632 A to Bernardi teaches a system that incorporates a microdialysis-based sensor. U.S. Pat. No. 6,605,048 B1 to Levin et al teaches a sampling device that incorporates a vacuum for the drawing up of a blood sample from the skin surface. None of these devices would permit ongoing delivery of a drug with simultaneous exposure of the sensor to interstitial fluid. Consequently, these systems are not compatible with continuous subcutaneous drug infusion.

Other sensor configurations utilize microneedles to reduce the invasiveness of the measurement technique, such as the invention that is the subject of 20060025717 to Zimmerman et al. However, the chief problem with microneedle arrays is the difficulty of keeping all the microneedles indwelled in mammalian tissue during body movement. Because microneedles are short in length, many of the needles will have a tendency to come out of tissue when the person moves suddenly or forcefully. This problem of unintentional explantation renders them unsuitable for extended use in an outpatient setting.

An application by Yang et al (US20160136357) discloses a unified hollow structure that can be used for analyte sensing and for drug delivery. Though insulin is specifically mentioned, this invention does not include any means of avoiding the oxidative interference from preservatives and does not include a method of avoiding the fragility of thin metal electrodes laminated to hollow structures. Similarly, a patent application US 20150374905 to Yodfat et al does not enable measurement of glucose in the presence of insulin preservatives and does not avoid the problem of fragility of thin metal electrodes.

In order to fabricate a combined sensor/catheter, one can incorporate biosensing elements into the wall of a hollow needle or catheter. The most obvious and simplest strategy would be to directly deposit metal (e.g. platinum, gold) indicating thin film indicating electrodes and thin film silver (Ag/AgCl) reference electrodes on the underlying polymer layer such as polyimide or polyester. One such design, disclosed in WO2002039086 to Ramey et al, incorporates printed electrode films. However, after carrying out many studies in animals, we have observed a major problem with sensing catheters made of thin film metal electrodes deposited over a polymeric layer. These sensors exhibited frequent delamination and general lack of durability.

SUMMARY OF THE INVENTION

At many bias potentials, insulin preservatives (phenol and m-cresol) in the vicinity of a glucose sensing indicating electrode create a large current (flow of electrons) which is not readily distinguishable from a high glucose level. More specifically, when an indicating electrode in the presence of the preservatives is polarized at a high bias potential, there is a large current even in the absence of glucose. For this reason, one method of reducing or eliminating the glucose-like current is to use a much lower bias potential. If a hydrogen peroxide sensing system is utilized, it is difficult to achieve a sufficient glucose current from peroxide oxidation while, at the same time, minimizing the interference that results from the insulin preservatives.

In contrast, if one utilizes certain systems such as osmium-based redox mediators that operate at a low bias potential, electrons can be transferred from glucose to an indicating electrode without interference from the insulin preservatives. In such a case, the mediator can be held in place by attachment to a polymer such as polyvinylpyridine or polyvinylimidazole which can be further crosslinked by bifunctional crosslinkers and immobilized at the sensor surface.

In addition to, or instead of, using redox mediator chemistry, a specialized filter can be used to trap the phenol and m-cresol before being delivered to the patient, thus preventing these compounds from reaching the subcutaneous space and causing an interference current. Because these filters prevent the phenol and m-cresol from reaching the subcutaneous space and from reaching the amperometric sensor, such filters can be used in combinations with sensors that employ conventional hydrogen peroxide detection, such as platinum-based sensors without redox mediators.

Regardless of whether a redox mediator or filter is utilized, the device will not function properly if the layers of the sensing catheter are not durable. For example, if thin metal films that make up the indicating electrode are deposited directly on to the polymer substrate, the electrode films will not be robust and durable. Instead, they will disintegrate and/or delaminate from the polymer during the usage period.

To avoid this fragility, and at the same time, minimize cost, it is necessary to laminate the thin metal electrode films to an underlying metal such as titanium. To be sufficiently robust, this metal must be substantially thicker than the electrode film.

BRIEF DESCRIPTION OF THE DRAWING

FIG. 10 shows the steps in which microfabrication is used to create the patterns for the electrodes and the interconnect traces. After titanium foil is laminated to polyimide, a layer of silver is sputtered over the titanium, followed by placement of a layer of photoresist. Some of the photoresist is selectively removed 18 in order to make unwanted silver available for removal by an etchant. After the remainder of the photoresist is removed, the silver electrode pattern is revealed 19. After the next coat of photoresist is applied, platinum is then deposited by sputtering 20. As the photoresist is removed, the unwanted platinum is lifted off, revealing the platinum electrode pattern 21. The next layer of photoresist is applied and removed selectively 22. Where photoresist is absent, it is possible to etch away unwanted titanium. As the photoresist is removed 23, the correct titanium pattern is revealed 23.

DETAILED DESCRIPTION

To reduce device burden, it is desirable to be able to measure glucose continuously at the direct site of insulin delivery, especially in subcutaneous interstitial fluid. In an attempt to better understand the response of an electrode or sensor in the presence of an insulin formulation, the experiment shown in FIG. 1 was carried out. This figure shows the responses of a platinum electrode (polarized at 600 mV vs a Ag/AgCl reference electrode) studied in phosphate-buffered saline (PBS). (For the purposes of definition, the term reference electrode in this disclosure refers to a reference electrode in a three electrode system or to a combined reference plus counter or reference plus auxiliary electrode in a two electrode system). The electrodes were bare, i.e. not coated with enzyme or an outer membrane. Early in the experiment, hydrogen peroxide ($H_2O_2$) was added and the electrodes responded briskly and maintained current in a stable fashion. At minute 13, a standard commercially-available insulin formulation (aspart insulin, Novo Nordisk) was added such that the concentration of phenol and m-cresol together (phenolics) was equal to 45 μg/ml. It can be clearly seen that there was a brisk oxidative (rising) current immediately after the insulin formulation was given.

However, the rise in current was transient and after a few minutes, it began to decline despite continued presence of the phenolics. At minute 23 and minute 33, more aspart insulin was given such that the concentration of phenolics became much higher, as indicated. It is important to note that no rise in current was seen after these later additions; instead, the current continues to decline such that the final current was markedly lower than the original current obtained from the $H_2O_2$ (which also remained in the solution). This progressive loss of current is due to poisoning of the electrode. More specifically, the phenol and cresol undergo a process of electropolymerization in which a thin layer of insulating polymer is formed on the electrode surface. This layer is largely impermeable to multiple analytes including $H_2O_2$, and for this reason, after exposure to phenolics, such an electrode is useless for the purpose of measuring glucose or other analytes.

Figure 1:
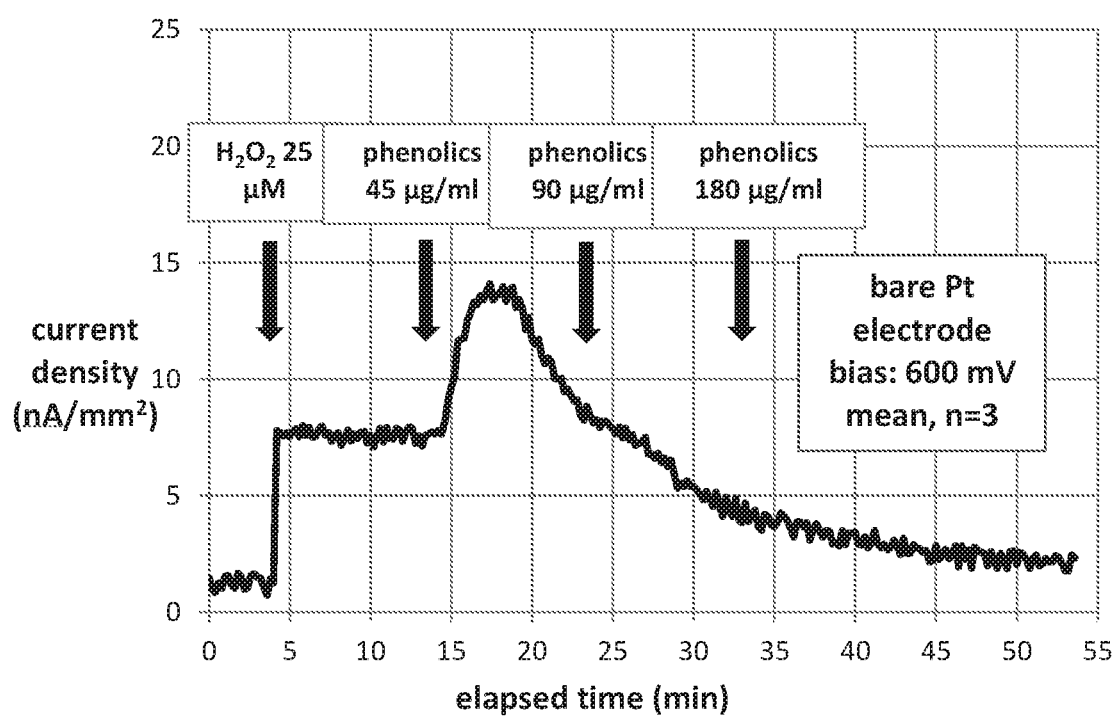
FIG. 1, a graph, shows the current obtained from a platinum electrode polarized at 600 mV. The initial response to hydrogen peroxide is normal and stable. The subsequent responses to ascending amounts of an insulin formulation containing phenolic preservatives initially display a positive (oxidative) response and later show a continuous decline of current, typical of electrode poisoning.

Another experiment (not shown) was carried out with insulin that does not contain preservatives (this preparation was branded Gibco and was purchased from Thermo Fisher Life Technologies). This insulin did not cause any electrochemical response and did not cause electrode poisoning. This experiment demonstrates that the interference noted in FIG. 1 is due to the preservatives, not the insulin per se.

Figure 2:
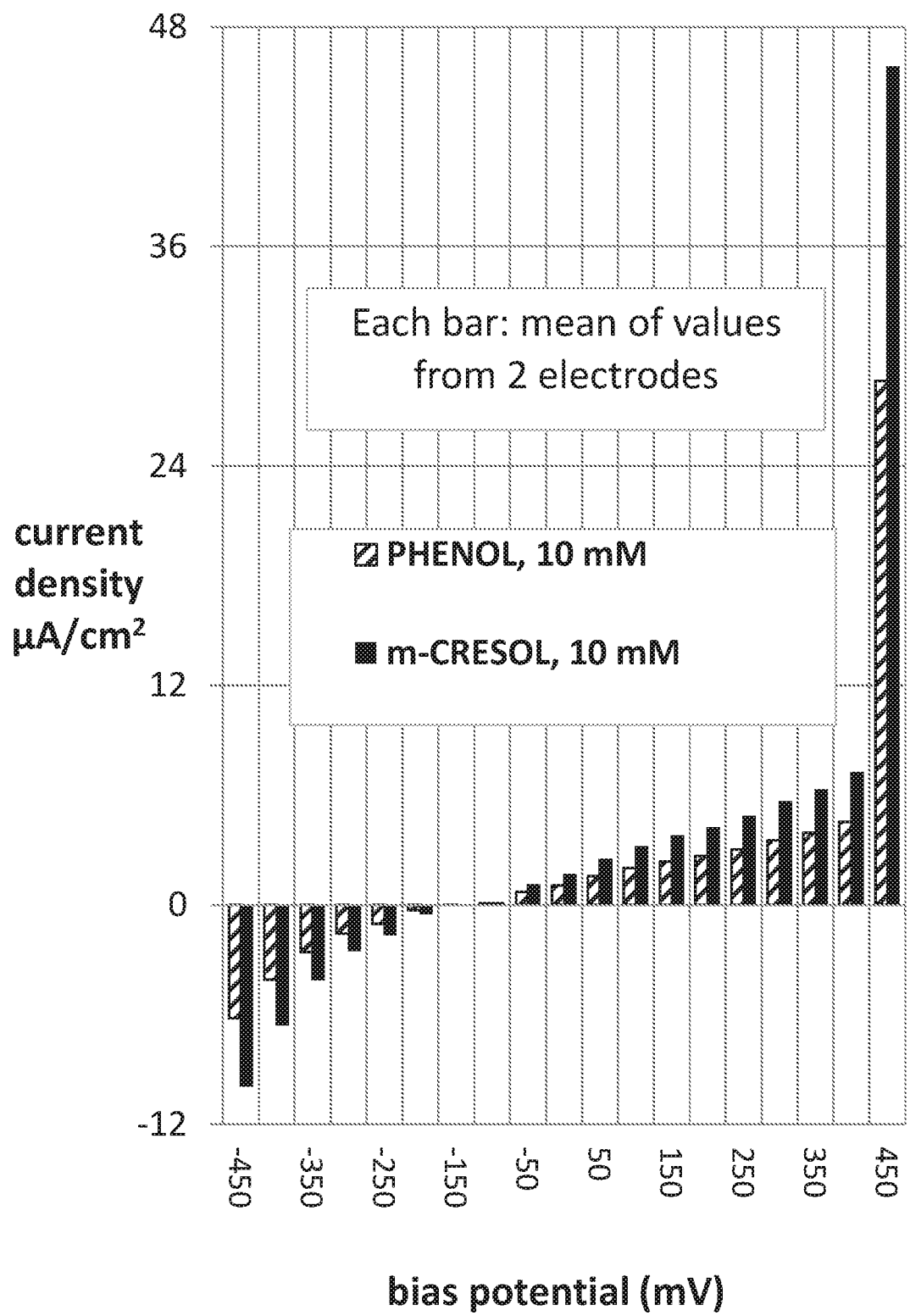
FIG. 2, a bar graph, shows the electrochemical effects of phenol and m-cresol on bare electrodes polarized at many different bias potentials. In particular, at high positive potentials typical of those used for peroxide detection, a very high oxidative current is observed. For both phenol and cresol, the oxidative current declines markedly as the bias potential is lowered. The appearance of such data obtained with platinum and gold electrodes is very similar. The data shown here are on gold electrodes.

We then decided to investigate the effect of the magnitude of the bias potential on the electrochemical response to the phenol and cresol, as shown in FIG. 2. In this experiment, bare gold electrodes were polarized at different potentials and exposed sequentially to phenol, 10 mM and to m-cresol, 10 mM. Electrodes were exposed to the phenolics for a very short period of time and were cleaned between tests to remove any electropolymerized polymer. The results showed that the responses to the phenolics are very dependent upon the magnitude of the bias potential. In particular, as the potential is raised to high potentials such as those over 350 mV, there is a very large oxidative response. In contrast, as the bias is lowered, particularly below 250, the response is quite low.

In an attempt to minimize the interference by reducing the bias potential, we carried out experiments using an osmium redox-mediated chemistry scheme very similar to that described in the early 1990's by the team of Heller and Ohara (Ohara T J, Rajagopalan R, Heller A. *"Wired" enzyme electrodes for amperometric determination of glucose or lactate in the presence of interfering substances. Anal Chem.* 1994; 66(15):2451-7).

Osmium complexes are suitable compounds for accepting electrons from glucose oxidase, more specifically from the prosthetic group of glucose oxidase known as flavin adenine dinucleotide (FAD). In one embodiment, the osmium is coordinated to a ligand such as, 4,4'-dimethyl 2,2'-bipyridine and also bound to the PVI polymer. Many other ligands can be used. The bond to the PVI prevents the osmium ligand from dissociating from the polymer backbone. Those skilled in the art will understand that electron donating groups such as methyl, methoxy or amino, when bound to the pyridine or imidazole ligands, will allow the osmium to transfer electrons at a lower polarizing bias. The term for the osmium and the pyridine or imidazole ligand complex is redox mediator. For optimal function, the redox mediator is bound to a polymer and this complex is known as the redox mediator polymer (RMP). Optimally, the RMP is crosslinked with agents such as glutaraldehyde or polyethyleneglycol diglycidyl ether, both of which link amine groups.

In one embodiment of the invention, the RMP is deposited on a gold indicating electrode, but other materials may be used, such as vitreous carbon, glassy carbon, graphite, platinum, or iridium. It is also possible to make the indicating electrode porous, for example by the use of acid anodization, laser poration, or plasma etching.

In one embodiment, the RMP is coated with a polymeric layer called the outer membrane. Oxygen permeability is not necessary for the function of this type of sensor, but a degree of glucose permeability is necessary. The outer membrane can be made of polyurethane, Nafion, poly(vinylpyridine), poly(vinylpyridine)-co-styrene, molecular weight cutoff polymeric membranes, silicone, hydrogels and many other materials that allow glucose permeation.

Figure 3:
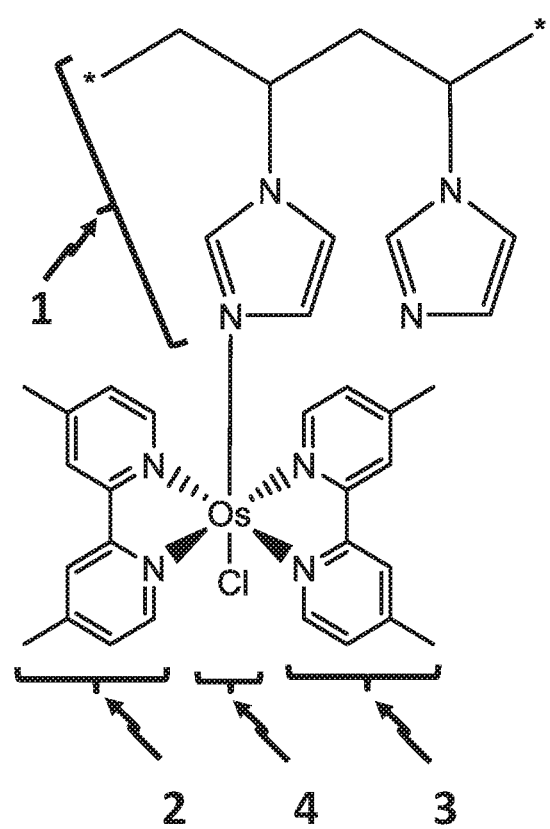
FIG. 3 shows the structural formula of the polymer repeat unit (poly(1-vinyl imidazole)) 1 bound to osmium 4 with two 4,4'-dimethyl, 2,2'-bipyridine moieties 2 and 3 (abbreviated PVI-OsDiMeBPY) in addition to one chloride remaining from the original osmium salt ligands.

For the exemplary experiments shown here, we utilized the osmium compound shown in FIG. 3. The polymer backbone 1 is composed of poly(1-vinyl imidazole) (PVI). Two coordination ligands, 4,4'-dimethyl,2,2'-bipyridine 2 and 3 are bound to osmium 4. The osmium 4 is bound to approximately one of every 5 to 15 imidazole groups on the PVI.

Figure 4:
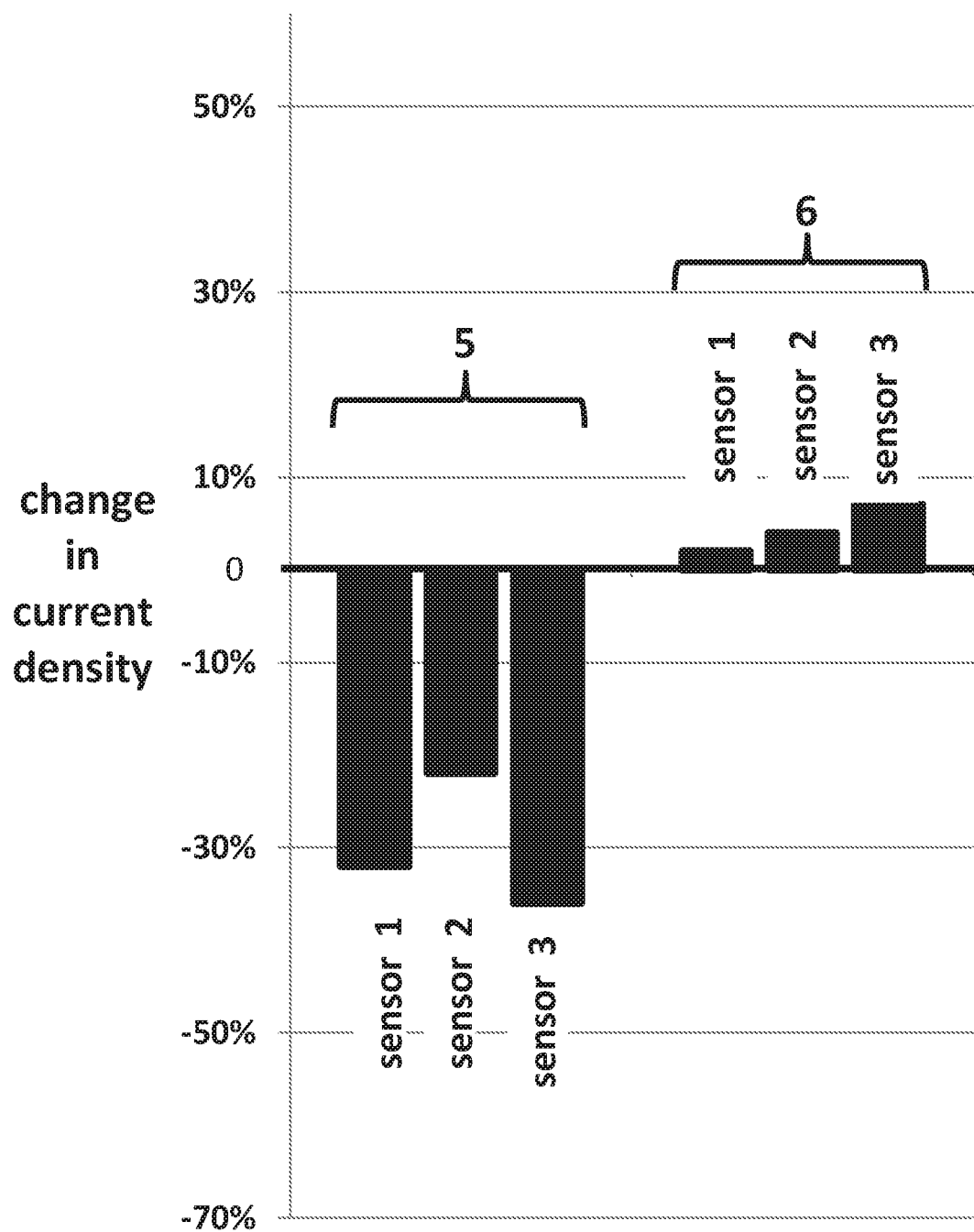
FIG. 4, a graph, compares the incremental change in current density of two types of glucose oxidase-based sensors after exposure to high dose mixed phenolics (total concentration 180 μg/ml, composed of equal parts by weight of phenol and m-cresol) over 20 minutes in the presence of glucose 5 mM. Over this period, there was a marked decline in current density 5 in each of the three platinum sensors. The bias potential of these sensors was 600 mV. In contrast, there was very little change in each of the three gold sensors 6 that were coated with glucose oxidase and PVI-OsDiMeBPY and biased at 180 mV.

Using RMP-based sensors and conventional platinum $H_2O_2$-sensing sensors, we then carried out the in vitro experiment shown in FIG. 4. In this experiment, gold sensors with coats of RMP, glucose oxidase, and an outer membrane were compared to platinum sensors coated with glucose oxidase and an outer membrane. The RMP-based sensors were biased at 180 mV and the platinum sensors were biased at 600 mV. After first being exposed to a 5 mM glucose solution, the platinum-based sensors 5 and the RMP-based sensors 6 were then exposed to ascending amounts of commercial aspart insulin formulation (Novo Nordisk) containing phenolics, as described for the earlier experiments shown in FIG. 1. FIG. 4 shows only the incremental response obtained at the highest concentration of phenolics, 180 µg/ml. Each bar represents results from a single sensor. It should be noted that there was a large negative response in the conventional platinum-based sensors 5 and only a small positive response in the RMP-based gold sensors. As discussed earlier, this large negative response lowered the response of the sensors to a point far below the original response to glucose (which remained in the solution), thus demonstrating a degree of electrode poisoning. As a follow up (not shown) to this experiment, both the platinum-based and RMP-based gold sensors were removed from the solution, rinsed and re-exposed to glucose 5 mM. The platinum-based sensors had a very low, nearly absent response to glucose (verifying permanent poisoning), but the response of the RMP-based sensors was brisk and nearly identical to the original response to glucose.

Figure 5:
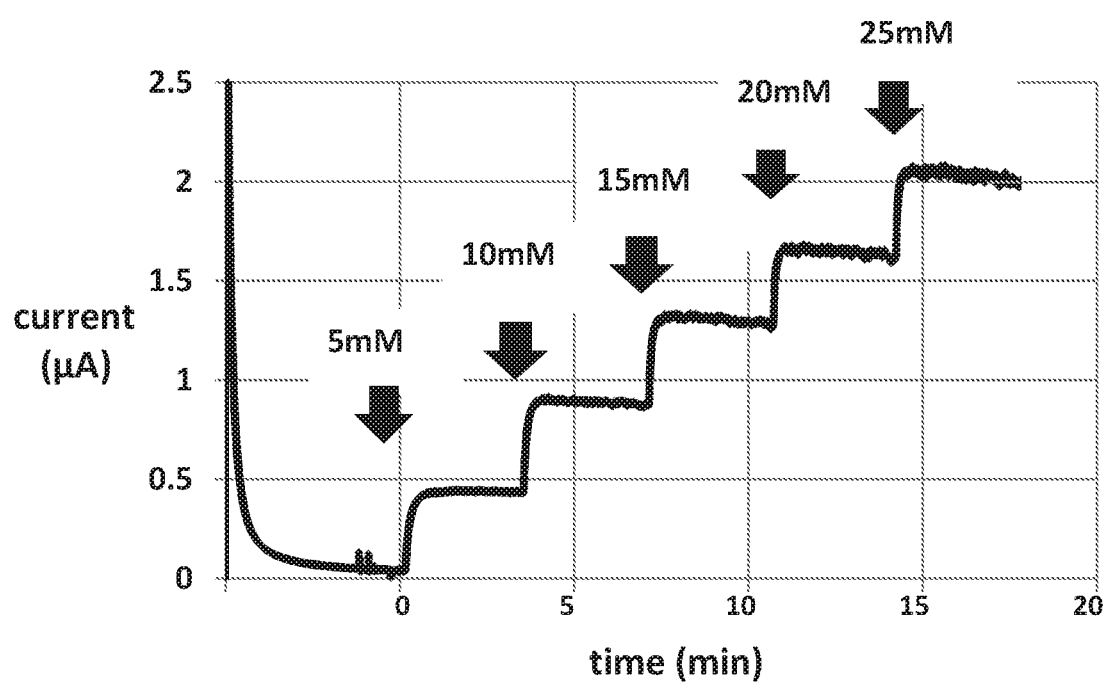
FIG. 5, a graph, shows a series of amperometric responses of a gold sensor coated with glucose oxidase and PVI-OsDiMeBPY, crosslinked with polyethylene glycol diglycidyl ether, to successive increases in glucose concentration in a solution of phosphate buffer sparged with Argon. The responses to glucose over this concentration range are largely linear.

FIG. 5 shows a response of a RMP-based sensor with a gold indicating electrode and a Ag/AgCl reference electrode to stairstep increases in glucose concentration in phosphate buffer during continuous Argon sparging. In this case, the RMP and glucose oxidase were crosslinked with polyethyleneglycol glycidyl ether but similar results were also obtained using glutaraldehyde liquid or glutaraldehyde vapor. Note that the response to glucose, up to at least 25 mM, is essentially linear.

The foregoing series of experiments demonstrate that a gold sensor, coated with RMP and crosslinked glucose oxidase and polarized at 180 mV vs Ag/AgCl, is able to measure glucose with little or no interference from the preservatives used in insulin formulations. In contrast, the use of a platinum sensor, coated with crosslinked glucose oxidase and polarized at 600 mV, undergoes an initial very large oxidation current when exposed to phenolics. Furthermore, if such exposure lasts for more than a few minutes, the electrode is consistently poisoned by a dense layer of electropolymerized phenolic compound that prevents $H_2O_2$ and other common analytes from reaching the indicating electrode and being measured.

Subcutaneous devices are exposed to many types of trauma, for example due to bodily motions and impacts typical of daily life. Therefore, even though the chemical layers over an electrode can successfully measure glucose without interference from phenol and cresol, a dual use sensing catheter will not function accurately for its entire usage period unless said catheter has a durable, robust construction.

One method of creating a continuous sensor built into the wall of an insulin infusion cannula is to laminate flexible thin metal films on the outer wall of a hollow tubular structure. However, if the choice of materials and processes are not carried out correctly, the resulting electrode layers will be very fragile. More specifically, if thin film metal electrode materials (less than 100 nm in thickness) are placed directly over polymeric surfaces (with or without underlying thin adhesion layers such at Ti, Au or Ni) the device becomes fragile. The electrode films often delaminate or disintegrate during impact, and therefore, such a device is not adequate for use as a catheter indwelled for days in the subcutaneous space. In fact, in such a design, substantial electrode delamination can be seen after only a few hours of in vivo use. In the experience of the inventors, whether or not a 25-200 nm tie (adhesion) layer is deposited under the electrodes, such a design leads to a frequent separation of the tie layer from the polyimide, frequent separation of the indicating or reference electrode films from the tie layer, and frequent fragmentation of the metal layers.

On the other hand, if a metallic foil is placed beneath the thin film metal electrodes, durability and fatigue resistance are markedly improved, while maintaining sufficient flexibility for fabrication and use as a biosensor. The use of the term "foil" indicates a metal layer that is at least 2 micrometers ($\mu$m) in thickness, that is, much thicker than the thin film layer typically deposited by sputtering, evaporation, printing or electroplating. Discussions of the beneficial mechanical properties of foils can be found in three scientific articles (Alzoubi, see above citation; Matsui Y, Ando N, Yoshida T, Kurotobi R, Matsushita T, Ohno K. *Modeling high adsorption capacity and kinetics of organic macromolecules on super-powdered activated carbon. Water Res.* 2011; 45(4):1720-8; and Lavvafi H, Lewandowski J R, Lewandowski J J. *Flex bending fatigue testing of wires, foils, and ribbons. Materials Science and Engineering.* 2014; 601:123-30). For these reasons, a metal foil (underneath the thin electrode film) is well-suited for the purpose of durability.

All layers of the sensing catheter must be tightly adhered to the adjoining layers. One method of creating interfaces with good adhesion and good durability is the use a laminating press at high temperature and high pressure. A high tack adhesive such as B-stage acrylate is located at the interface of the foil and underlying polymer and adheres the two materials together. After the lamination, thin film electrode materials can be deposited over the durable metal foil. The thickness of the metal foil is typically 2-15 $\mu$m.

The metal of which the foil is composed must be chosen carefully. In the case of an amperometric glucose sensor, the indicating electrode is typically platinum, gold or carbon. Copper (which is commonly used as the foil for flexible electronic circuits), is not suitable for use in a biosensor. Specifically, if there is concurrent physical contact between interstitial fluid, copper and platinum, a large galvanic current will occur as a result of the junction of dissimilar metals. A suitable candidate for the foil is titanium, which is inexpensive and which we found to cause little to no galvanic current when paired with platinum. Silver and copper are not suitable as this foil material. Gold is of intermediate value.

Using the durable sensing catheter design discussed above, we carried out a series of studies in non-diabetic Yucatan mini-pigs of weight 33-60 kg. In preparation for this study, sensing catheters were fabricated. A polyimide strip, 12.5 $\mu$m in thickness, was laminated with a sheet of titanium foil, 5 $\mu$m in thickness. Three thin film 1 sq mm platinum indicating electrodes and a Ag/AgCl reference electrode were sputtered on to the titanium foil surface. This electrode strip was wrapped around, and laminated to, the outer surface of a blunt, hollow 21 gauge stainless steel tube with the aid of an epoxy adhesive designed for use in high salt moist environments. The indicating electrodes were coated with glucose oxidase and bovine serum albumin (BSA) (in a ratio of 3:2) and crosslinked with glutaraldehyde vapor, then coated with a silicone-polyurethane copolymer outer membrane (Lubrizol, Inc). The term used for such a dual use device is a "glucose sensing catheter" or "sensing catheter." A series of interconnect traces emanate from the three indicating electrodes and the single reference electrode and terminate in a body-worn electronic sensor module which is in electrical continuity with the sensing catheter. The sensor module contains a battery and a Bluetooth-enabled transceiver, which transmits the electrochemical signals to a personal computer or mobile phone.

Multiple sensing catheters, attached to telemetric sensor modules, were inserted in the subcutaneous tissue of the pig's abdomen under isoflurane anesthesia. The sensor module was adhered to the skin with cyanoacrylate glue, then each pig was allowed to recover from anesthesia. The next morning, the animal was again anesthetized with isoflurane. After a stabilization period, a euglycemic clamp was carried out for 5 hours. More specifically, an infusion of 20% dextrose was given intravenously according to a computerized algorithm in order to avoid hypoglycemia. At minute 105 during the clamp, as indicated by the arrow in FIG. 6, lis-pro insulin (0.22 units per kg total dose, divided between two catheters, so that 0.11 units per kg was delivered through each catheter) was given through some sensing catheters. Insulin was not delivered through other sensing catheters.

Figure 6:
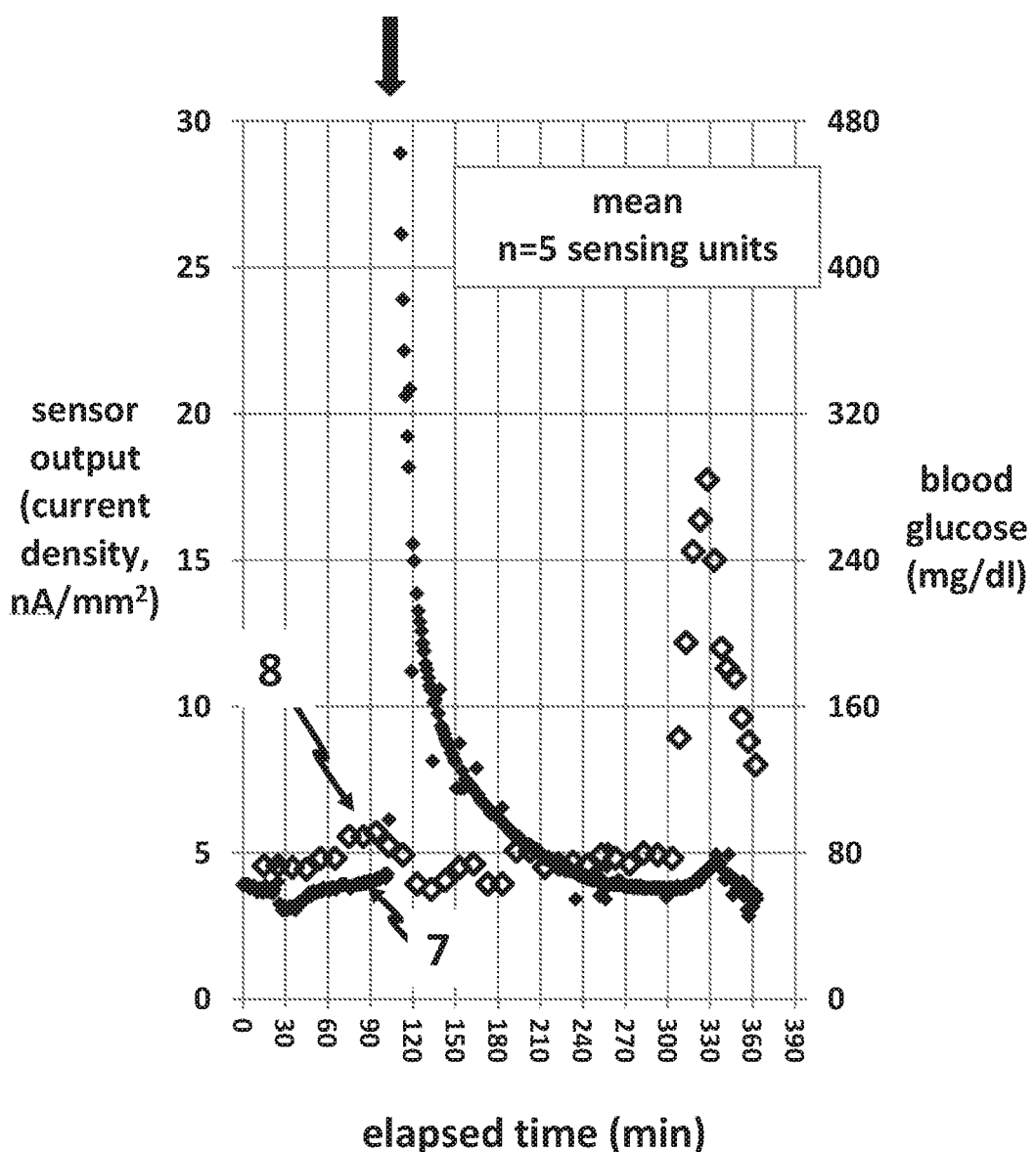
FIG. 6, a graph, shows the amperometric signal 7 (small closed symbols) and glucose levels 8 (large open symbols) obtained in pigs from a glucose oxidase-based hydrogen platinum sensor biased at 600 mV. When lis-pro insulin was given at minute 105, the preservatives in this formulation led to an immediate very high oxidative response followed by electrode poisoning. The poisoning is evident toward the end of the experiment when the amperometric signal is minimal despite very high glucose levels.

FIG. 6 shows mean exemplary data obtained from several sensing catheters through which the lis-pro insulin was delivered. The electrochemical sensor current 7 and the blood glucose values 8 (measured in duplicate by a Bayer Contour Next meter) are shown by arrows. Note that immediately after the insulin was given, there was a very large current spike with a fast exponential decline. Late in the experiment, at minute 300, a rapid infusion of 20% dextrose was given intravenously, leading to a marked rise in blood glucose to a level of almost 300 mg/dl. It can be seen that the sensors were unable to respond vigorously to this marked rise in glucose level. There was only a very small rise in current during hyperglycemia, typical of sensors that had undergone electrode poisoning. Many such experiments were carried out in pigs. In summary, in about 40% of the experiments in which lis-pro insulin was given, there was a marked oxidative rise in current between minutes 105 to 165, despite the fact that glucose was being held steady. It is likely that in these cases, the insulin formulation, after leaving the catheter, flows back on to the sensor elements, causing an oxidative signal. In the other cases, it is likely that the insulin formulation flows away from the catheter without contacting the sensing elements, thus failing to cause an interfering signal.

Figure 7:
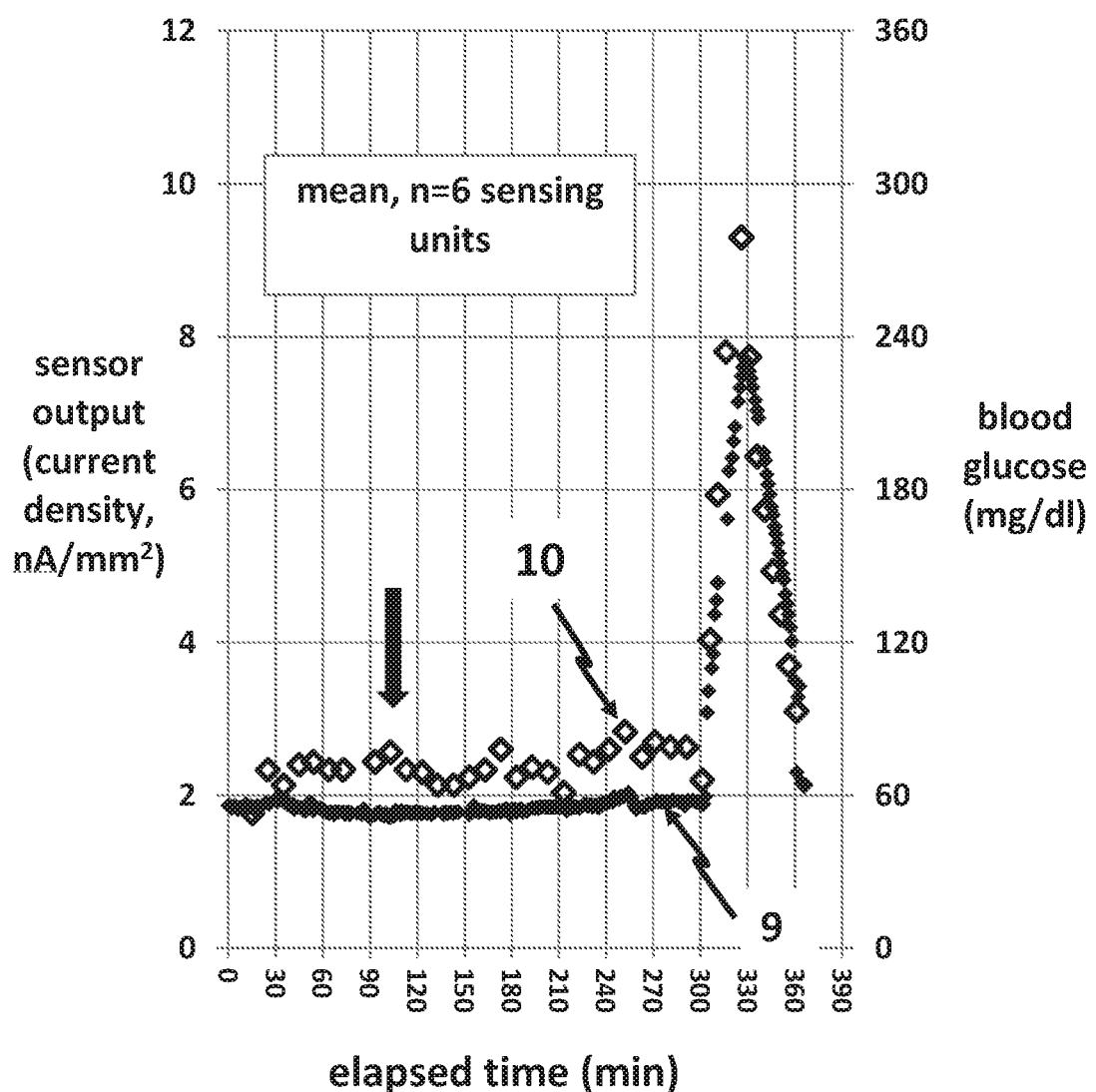
FIG. 7, a graph, shows the amperometric signal 9 and glucose levels 10 obtained in pigs from a gold-based sensor coated with glucose oxidase and PVI-OsDiMeBPY, crosslinked with glutaraldehyde, biased at 180 mV. Lis-pro insulin was given at minute 105, and despite a high level of preservatives in this formulation, there was no change in the amperometric signal 9. Notable is the brisk rise of the current 9 over the final hour of the experiment in response to marked hyperglycemia, verifying absence of electrode poisoning.

Other pig experiments were carried out with sensing catheters with gold indicating electrodes and RMP (PVI osmium 4,4'-dimethyl 2,2'-bipyridine) bound to glucose oxidase by glutaraldehyde. FIG. 7 shows mean data from several RMP-based gold sensors through which lis-pro insulin was delivered. Consistent with the in vitro data discussed above, there was little to no evidence of interference from the insulin preservatives after the insulin formulation was given. Sensor current 9 did not rise at minute 105 when lis-pro insulin was given. Furthermore, the RMP-based sensors responded vigorously to the marked hyperglycemia during the last hour of the study. Note that blood glucose rose briskly during the last hour of the study. During this rise, the brisk rise in current 9 verified absence electrode poisoning.

Figure 8:
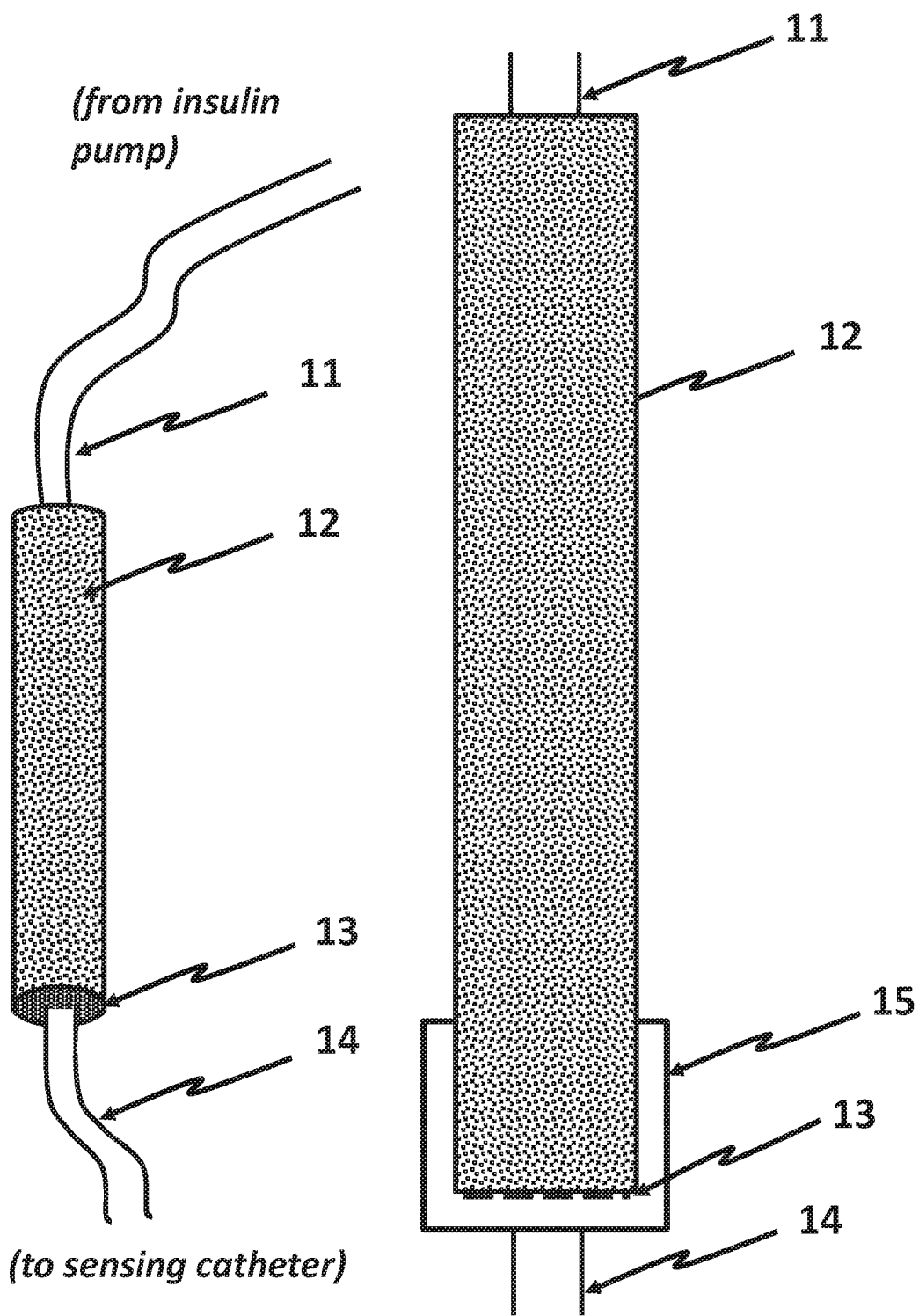
FIG. 8 is a drawing of an in-line filter that removes phenolics from an insulin infusion line. The proximal feed insulin line 11 brings insulin formulation from an insulin pump and is connected to the proximal end of the filter 12. A protective membrane 13 prevents the filter material from entering the insulin exit line 14 located at the distal end of the filter. A zoomed-in view on the right panel also shows a cylindrical retainer 15 which holds the protective membrane 13 and the exit line 14 firmly on to the distal end of the filter 12 without blocking the passage of insulin.

We also discovered another means of avoiding the preservative-induced oxidative current: the use of filter that is placed in the insulin infusion line. U.S. Pat. No. 5,936,061 to Andersson et al, taught the use of hydrophobic Zeolite filtration to remove insulin preservatives from an insulin formulation vial prior to injection. In an embodiment of the current invention, we teach the use of in-line filters designed to be used by persons with diabetes who use portable insulin pumps that deliver insulin subcutaneously. Such a filter is depicted in FIG. 8. The plastic tubing that comes from the insulin pump 11 is attached to the filter cartridge 12 that is filled with filter material. At the distal portion of the filter cartridge is a protective membrane 13 that prevents filter beads or particles from being released into the insulin tubing (and thus into the body of a patient). One such embodiment for this protective membrane is porous cellulose acetate, the pore size being smaller than the filter bead material. Many other membrane compositions and many pore sizes are suitable in the fabrication of the protective membrane. Tubing 14 brings the filtered insulin out of the filter cartridge into the sensing catheter. On the right panel of FIG. 8 is shown a zoomed-in figure of the filter with additional detail. Typically, it is necessary to utilize a retainer unit 15 that holds the filter cartridge 12, the protective membrane 13 and the exit tubing 14 firmly in place. In some embodiments it is also desirable to place a retainer unit at the proximal end of the filter.

There are many such bead or particle materials that can be used to filter the phenolics out of the insulin formulation. Some of these materials include those typically used for size exclusion chromatography, also known as gel filtration chromatography and molecular sieve chromatography. For the purposes of this invention, size exclusion media are defined as particles containing pores that trap smaller molecules and allow larger molecules to readily pass through. In the case of one embodiment of this invention, preservatives contained in insulin formulations, including m-cresol and phenol, are trapped within small pores. The larger insulin molecules, which are not trapped, pass readily through the filter.

One suitable filter material is crosslinked dextran, one brand of which is Sephadex®. Sephadex G10 is suitable since it is intended to separate compounds smaller than 700 Daltons from those larger than 700 Daltons. This grade of crosslinked dextran is suitable because cresol and phenol weigh about 100 Daltons, whereas insulin and insulin analogs weigh about 5800 Daltons. Other grades of crosslinked dextran can also be used. In addition to dextran, other choices for filter materials include carbon (including charcoal and activated carbon), alumina, silicates, silica, mixtures of alumina and silica knows as Zeolites, and other compounds used to separate compounds based on molecular size. It is also possible to use materials typically used in reversed phase high performance liquid chromatography to separate molecules on the basis of hydrophobicity/hydrophilicity. Phenol and cresol are more hydrophobic than insulin.

Figure 9:
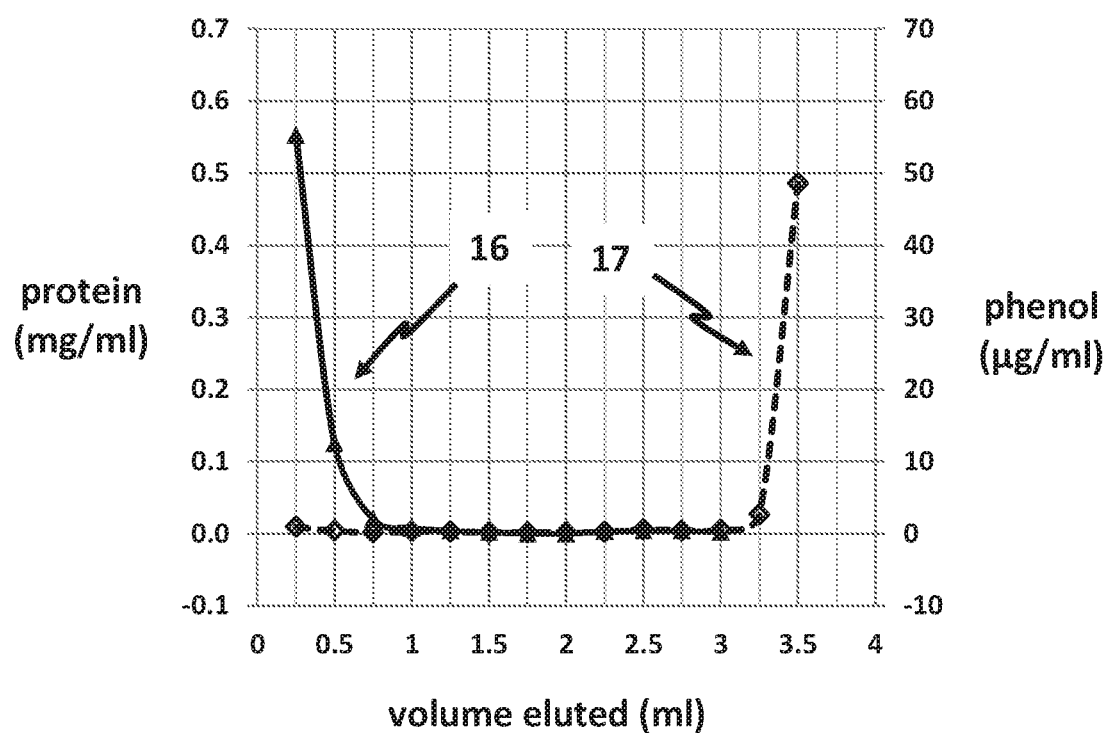
FIG. 9, a graph, demonstrates the effectiveness of the filter that removes phenolics. Aspart insulin was placed on the proximal end of the filter. Many samples (each 0.25 ml in volume) were then collected during delivery of phosphate buffer (in 0.25 ml units). Results of an assay for insulin 16 (as estimated by measurement of total protein using a bicinchoninic acid [BCA] assay) are quantified on the left axis and results of an assay for phenol 17 (using a nitroprusside-based assay) are quantified on the right axis. The filter material is Sephadex G10 (medium). Insulin passes through the filter very soon after delivery and the phenolics come out very late, only after 3 ml has passed through the filter.

FIG. 9 shows results of an experiment carrried out in order to separate aspart insulin from its preservatives. A filter similar to that shown in FIG. 8 was fabricated using Sephadex medium G10 beads, 40-120 µm (GE Healthcare, Inc). Ten units of aspart insulin were placed on the column, which was 3 mm in diameter and 64 mm in length. Subsequently, 0.25 ml of PBS was delivered by an insulin pump every 5 minutes and an equal volume of eluent was collected every 5 minutes. The eluent was assayed repeatedly for insulin by using a BCA total protein assay (trace 16 in the figure). Phenol was assayed repeatedly using a nitroprusside-based assay with a spectrophotometric end point (trace 17). The results show that the insulin elutes very early in the experiment with little to no more insulin coming out after the second collection. In contrast, phenol does not elute until late in the experiment after 3 ml have been collected. These results demonstrate that this embodiment of the invention will work well for persons with diabetes who use an insulin pump. The insulin reservoirs for currently-available pumps contain up to 3 ml of insulin formulation. Thus, for pump users who use such a filter, the phenolics will not appear during the usage period of 3 days during which no more than 3 ml of insulin formulation can be administered.

A variation on the use of a filter material is to electrically connect to the filter material and remove interfering substances electrochemically. As an example, activated carbon filtration particles packed and immersed in a saline solution are conductive; thus the carbon can be used as an indicating electrode, polarized at 400-800 mV by a power source vs a suitable reference electrode such as a Ag/AgCl electrode. In such a case, to avoid a short circuit, the reference electrode cannot be touching the carbon and so a sheath can surround the reference electrode. The sheath prevents contact with the carbon and the saline allows electron flow to complete the anode-cathode circuit. The carbon, when suitably biased, oxidizes and electropolymerizes the phenol and m-cresol rather than allowing their passage through the filter. In such a filter, some of the phenolics may adsorb normally on to the carbon, while at the same time, other phenolics are electropolymerized to a thin layer of plastic which stays on the carbon in the disposable filter. The use of electropolymerization and adsorption is more efficient than adsorption alone.

It is important to note that there are many physical forms that the filter could take other than the single long tubular structure shown inn FIG. 8. For example, it is possible for the filter to loop back on itself many times in a serpentine fashion. Such a design would not take up as much longitudinal distance.

For use in a person with diabetes, the filter can be placed anywhere in the insulin delivery line, such as in the insulin reservoir (which is usually situated with the pump body), the insulin tubing, or the insulin fluid path within the skin worn sensor module immediately proximal to the entry of the fluid into the sensing catheter.

When a filter is used, it is possible to use a higher polarizing potential bias in order that the sensing system can utilize standard sensing of hydrogen peroxide. In such a case, there is no need for a redox mediator. To optimize the signal from hydrogen peroxide oxidation, a high bias such as over 500 mV is typically used. Alternatively, one can use the filter in combination with a redox mediated system with a lower bias. Such a combination has the advantage of using two effective methods in order to markedly reduce the adverse effects of phenol and cresol during CGM.

The above description teaches the use of a filter used to remove phenolics from an insulin delivery line after the insulin formulation is placed in the pump reservoir but before insulin is pumped into a dual use sensing catheter. However, it should also be noted that such a filter can be used in a standard insulin infusion set (without a glucose sensor). It is important to note that there are many toxic effects of phenol and m-cresol. These compounds have been associated with cancer, especially bladder cancer {Garrett, 1975 #3}. The US Environmental Protection Agency cites associations between phenolics administration and weight loss and neurotoxicity {(IRIS), #2; Agency, 2002 #12} and has classified m-cresol as category C (possible human carcinogen). In addition, these compounds have been associated with many other adverse effects including inflammation at the site of insulin delivery {van Faassen, 1989 #10; van Faassen, 1990 #9}). More recently, phenolics have clearly been shown to be cytotoxic to mammalian cells {Weber, 2015 #17}.

For these reasons, many people who take insulin may decide that they do not want to be exposed to the high concentrations of phenolics that are in all formulations of insulin intended for human use. Therefore, even in the absence of a sensing catheter, the insulin infusion set with phenolics filter is a useful invention applicable to those persons who use an infusion pump. For those who do not use an insulin pump, it is possible to use the same filtration materials to remove phenolics from commercial insulin formulations before administering the drug by injection.

Example 1: Redox Mediator-Based Sensing Catheter

Laminate Metal Foil to Polymer Substrate:

Purpose: This step creates a laminate of titanium and polyimide (Ti/Pi). In this example, the Ti thickness is 5 μm and the polyimide thickness is 12.5 μm, though these dimensions should not be construed as limiting. This example creates a laminate rectangle whose dimensions are 60 mm×85 mm.

Materials include Deionized water; Polyimide sheet w/ B-stage acrylate adhesive; Titanium foil; press pads; Teflon sheets, and graphite press plates, Heated hydraulic press capable of achieving 400 deg F.;

Plate setup process: Between the caul (pressure-applying) plates of the hydraulic press, materials should be stacked in the following order, from bottom to top: Graphite press plate; press pad; Titanium foil; Polyimide, with B-stage adhesive facing titanium foil; press pad; Graphite press plate.

Prepare graphite plate, graphite foil, and Teflon sheets prior to handling polyimide and titanium. All sheets should be cut to the size of the caul plates and cleaned with isopropyl alcohol (IPA), followed by careful inspection for lint or contaminants.

For operation of the press: Place plate stack into hydraulic press and apply 5000 lb of force to caul plates. Set temperature setting to 375 deg F. for both top and bottom plates. Once both caul plates reach 375 deg F., set press to 15000 lb and leave in place for 1 hour. Allow caul plates to cool to under 100 F, then remove plate stack from press.

General Equipment and Supplies (for all following steps): Double-sided polyimide tape; plastic card; razor blade; 50×75 mm glass slide; isopropyl alcohol (IPA); deionized (DI) water; Pt (platinum) target; Ag (silver) target; aluminum foil; Ar (argon) plasma etcher; quartz crystal microbalance (QCM); sputter tool; hot plate; mask aligner—e.g OAI 200 tabletop mask aligner; spin coater capable of 300 RPM; argon source.

Prepare Ti/Pi Laminate for Application of Gold and AG Electrodes

Clean glass slide using soap and tap water, IPA wash, DI rinse, Ar plasma clean for 1 minute; dry. Place double sided polyimide tape on hot plate. Apply polyimide tape, remove bubbles. Place aluminum foil on hot plate; apply double sided polyimide on slide and place rigid backer adhesive side up. Apply Ti foil to rigid backer. Apply Ti/polyimide plus rigid backer to the polyimide tape. The stack order should be (bottom to top): glass slide, double sided polyimide tape, rigid backer, Ti/polyimide laminate with Ti side up.

Deposition of Silver Film

Purpose: To deposit a layer of Ag (later chloridized to Ag/AgCl) in order to create reference electrode. The nominal thickness is 400 nm in order to allow for a reasonable thickness of Ag/AgCl after chloridization (chloridization reduces the thickness of Ag). In this process, silver sputtering is used, but other methods such as thermal evaporation, printing, or electroplating can also be used. Materials required include: Treated 50×75 mm Ti/PI sheet on glass slide, sputter unit such as CRC-100, Ag target, and Ar compressed gas.

In order to sputter Ag layer, the substrate is placed in the sputter unit, and the vacuum pumps degas any exposed adhesive. The sputter chamber is filled with Ar, the operator allows system to equilibrate to 7 mTorr. Sputter until Quartz Crystal Microbalance (QCM) reading is 5.00 kA (500 nm) of Ag. (Gain=75, Density=10.5, Z-ratio=0.529, Tooling Factor=256). Remove device from sputter unit. Tape test in a corner with 3M Magic Scotch tape to ensure good adhesion. Store in a dust-free covered container.

AG Patterning and Etch (Remove Unwanted AG).

For drawings of the main microfabrication (electrode patterning) steps, see FIG. 10. Purpose—To pattern photoresist for Ag pads on Ti/PI substrate. Materials: 50×75 mm Silver sputtered Ti/PI substrate on glass slide; NaOH pellets; 300 mL beaker; 250 mL beaker; optical mask, S1813 (photoresist); 80/20 primer (80% Propylene Glycol Monomethyl Ether Acetate and 20% Hexamethyldisilazane (HMDS) primer). Materials for clean room use include the Mask aligner; Spinner; hotplate; DI water; scale; S1800 series photoresist; NaOH (pellets or solution).

First, carry out the general photoresist process that is included below. Then mix Ag etch solution. Add 75 mL of 3% USP grade $H_2O_2$, then 8 mL laboratory grade 30% ammonium hydroxide to a crystallizing dish. Immerse patterned substrate in solution for 30 seconds, gently agitating. Bubbles will not form when the reaction is complete. Rinse with DI water and blow dry with nitrogen gas or Argon. Remove photoresist with 0.3M NaOH solution.

AU Patterning, Sputtering, and Liftoff

Purpose: To pattern Au pads on Ti/PI/Ag substrate. Materials include: 50—75 mm Silver sputtered Ti/PI substrate on glass slide; NaOH pellets; 300 mL beaker; 250 mL beaker; optical mask; S1813 primer; Ti/PI/glass with Ag deposited on surface; 80/20 primer, as detailed above; Ag etch film mask; 3 mL pipette; Acetone; isopropyl alcohol (IPA); crystallizing dishes; graduated cylinder; timer.

Carry out general photoresist process that is included below. Clean under Ar for 1 minute. Activate vacuum system. Sputter 90 nm (0.900 KA) Pt. Sputter 50-90 nm of Au (Density=19.3, Z-ratio=0.381). Use Scotch tape to entirely cover the substrate. Press down firmly across the substrate, then slowly remove in order to remove Au layer. Inspect tape test sheet for any failures in Au adhesion. Use an additional piece of tape to remove any bridges between Au pads. Remove photoresist/remaining Pt/Au by tape method (3m magic tape over entire array), then sonicate in 0.5M NaOH. If any bridges remain, gently scrub using Kimwipe while in solution.

Titanium Etch (Remove Unwanted Ti in Order to Create Electrical Interconnects)

Purpose: To define and separate titanium traces on sensor. It is important to prevent titanium that underlies an indicating electrode or an indicating electrode interconnect trace from contacting titanium that underlies other indicating electrodes/traces or contacting titanium that underlies reference electrodes/traces. Materials include Ti/Pi mounted slide; titanium etchant; 400 mL beaker; crystallization dish; DI water; NaOH, Ultrasonic cleaner.

Carry out general photoresist process that is included below. Prepare etchant bath. Place substrate in etchant solution and observe closely, rinse with DI water when etch is complete.

Rinse with DI water and blow dry with nitrogen gas or argon.

Prepare Sensors for Human use: Individualize, Wrap, Chloridize, Apply Protective Coat to Reference Electrode, and Clean Indicating Electrodes Individualize each tri-electrode strip using mechanical or photonic means such as UV laser (wavelength: 405 nm).

Wrap the electrode strip around a 21-25 gauge stainless steel needle (sharp bevel on end) or blunt tube. Electrode strips are wrapped axially around the needle/tube and adhered using epoxy or other biocompatible adhesive. If a blunt tube is used, a sharpened stylet within the tube is utilized in order to pierce the skin upon insertion. (The stylet is later removed, allowing drug delivery via the lumen of the tube).

Ferric chloridize with 50 mM $FeCl_3$ for 5-10 min. ALTERNATIVE: Electrochloridize at 0.6 V×10 min using power supply configures so that the Ag is the Anode (+) and Pt is the cathode (−). Bath for electrochloridization is KCl and HCl, both 0.5 M.

Voltage cycle (clean) indicating electrodes in 1×PBS, −1.5 volts×5 min, 1.5 volts×5 min, −1.5 volts×5 min. Verify presence of evolving bubbles at sites of electrodes.

Application of redox mediator polymer and glucose oxidase to surface of gold indicating electrode. In this example, the redox mediator polymer listed is Poly-(1-vinyl)-imidazole.Osmium-4,4'-dimethyl-2,2'-bipyridine. However, there are such compounds that can be used, either with pyridine or imidazole-based osmium ligands and with poly vinylpyridine, poly vinylimidazole or other polymers as the backbone.

Before beginning this step, gold tri-electrodes have been wrapped, cleaned, and chloridized.

Using DIW as a solvent, prepare 1 ml of both of the following solution: redox mediator polymer (10 mg/ml) and glucose oxidase, 100 units per mg (10 mg/ml). Combine 40 uL of the redox mediator solution and 10 uL glucose oxidase solution. When dispensed manually, one can draw up this mixture into 1 mL plastic syringe with 30 gauge needle and carefully position tip of needle over center of each of the three electrodes, then dispense a small drop (1 ul) on each electrode without coating the reference electrode. After partial drying, one can apply a second layer of the mixture. Alternatively, one can use a microdispensing unit such as ink jet printer, being careful not to heat the enzyme to over 50 deg C.

Place the holder upright within a glutaraldehyde vapor chamber (25% glutaraldehyde) for 30 minutes, then let cure for 30 min at room temperature.

The outer membrane deposited over the entire shaft including indicating electrodes and reference electrode can be one of many glucose permeable polymers, including polyurethane, silicone, combined silicone-polyurethane, or other polymer. One effective outer membrane is Poly-(4-vinyl or 2-vinyl) pyridine co-styrene (10-30% styrene, PVP-S) 64 mg/ml, in anhydrous ethanol. One can deposit this polymer manually, by using a automated dip-coater, using an ink jet printer, micro-contact printing, or by using other precise method of dispensing. Coat the outer membrane material on the entire sensor shaft. Dry for 15 min at room temp.

After drying, it is possible to test the sensor in solutions of glucose, interfering compounds, etc.

Assemble into Electronic Module that Serves the Purposes of Telemetry and Application of Polarizing Bias:

Insert the sensing catheter into a battery powered telemetry module (such as a low energy Bluetooth module such as that marketed by Nordic, Inc).

For the redox mediator polymer approach discussed above, a potential bias of 180 mV is suitable. A low bias such as this largely avoids the signal artifact resulting from oxidation of insulin preservatives (phenol, m-cresol) that would be seen if a higher bias were used. A low bias also avoids the problem of electropolymerization that is routinely seen with the use of higher bias potentials. When larger bias potentials are used, the cresol and/or phenol undergo the process of electropolymerization which deposits a cohesive thin layer of insulating plastic on the electrode. This layer of plastic reduces or eliminates the ability of osmium from communicating with the electrode materials and also reduces transport of molecules such as hydrogen peroxide to the surface of the indicating electrode.

Sterilization:

Expose to e-beam, gamma irradiation, ethylene oxide or activated glutaraldehyde sterilizing solution.

Attach to Insulin Pump and Operate Device:

After priming with insulin, an infusion line from an insulin pump (e.g. Medtronic Minimed, Animas Ping, Tandem t-slim, Roche Spirit, etc) is attached to the sensing catheter (which is located in subcutaneous tissue) and insulin is delivered. The constant pressure head from the fluid infusion line prevents fluids from coming back out of the body. In order to be displayed to the user, the glucose concentration or the electrical current or voltage data representing glucose concentration is obtained from the sensor. These data are transmitted by Bluetooth or other wireless protocol to the display of the insulin pump, to a computer, to a dedicated medical device, or to a cell phone. Storage of data can be carried out on any of these devices or on the body worn electronics unit that directly interfaces with the subcutaneous sensing catheter. An advantage of storing the glucose data on the body-worn unit is that the data are not lost if the receiving unit is lost or out of range.

General Photoresist Process (Common to Multiple Steps).

Materials: 50×75 mm Ti/PI substrate on glass slide; NaOH pellets or solution; 300 mL beaker; 250 mL beaker; optical mask; photoresist. 80/20 primer as defined above.

Method: Mix 200 ml 0.1M NaOH (8 g/L w/ pellets or 15 mL/L w/ 10M solution) primary developer in glass dish. Ensure that solution is well mixed, especially if using NaOH pellets. Mix 0.075 M NaOH secondary rinse in glass dish. Ensure that solution is well mixed. Spincoat 3 mL 80/20 primer with standard method—10 seconds @ 1000 RM followed by 30 seconds @ 3000 RPM. Bake for 3 minutes @ 85 C. Spin coat three layers of photoresist with standard method. Bake substrate for 1 minute at 85 C between each spin step. Expose for 180 s @ 600 W. Bake for an additional 60 seconds. Develop in 0.1 M NaOH developer, gently agitating. Rinse in secondary bath for 10 seconds. Dry with nitrogen gas, inspect for developed regions with remaining resist. (Exposed regions should appear uniform across the entirety of the substrate. Properly cleaned regions will gain a faintly white appearance as they go from wet to try if no photoresist remains on the surface). Bake for 10 minutes and allow to cool. If regions remain, immerse in primary and secondary baths for an additional 5 seconds and check again. If substantial regions remain, air dry, clean with 0.3M NaOH, and return to step 4. Check process parameters.

Example 2: Filtration Using a Platinum Indicating Electrode with High Bias Potential Many aspects of this example are the same as in Example 1. However, instead of Au being deposited, Pt is deposited by sputtering, using these sputter settings: Density=10.5, and Z-ratio=0.529.

No redox mediator is used. Glucose oxidase is applied along with a protein extender, bovine serum albumin. Glutaraldehyde crosslinker is used to link the amine groups of glucose oxidase and albumin and the weight ratio of glucose oxidase:albumin:liquid glutaraldehyde is between ranging from 6:4:5 and 6:4:1. The mixture applied to the Pt electrode is dried for at least 10 min at 40° C. Additional layers can be deposited to increase sensitivity to glucose. In such a case, dry the final coat for at least 20 min. Then rinse in stirred DIW for 10-15 minutes to remove unbound enzyme. Deposit two coats of outer membrane composed of 1.5-2.5% w/v polyurethane (PU) or copolymer of silicone and polyurethane deposited on the indicating electrode(s) and reference electrode(s). Vendors such as AdvanSource Biomaterials, Lubrizol, or DSM Polymers make such polymers. The proportion of silicone is used to regulate oxygen permeation; and polyethylene oxide or poly ethylene glycol moieties or other polar moiety is used to regulate glucose permeation. A suitable solvent is a mixture of THF and DMAC (25:75, V/V). Dry each PU coat×20 min at 40 deg C. Keep solvent and polymer/solvent dry with molecular sieves 3A or 4A.

A suitable material for the filter is Sephadex G10, which is rated to separate compounds with molecular weights above 700 Da from those below 700 Da. A suitable tubular structure of approximately 3 mm in internal diameter and at least 64 mm internal length is filled with the Sephadex medium G10 beads, size 40-120 µm. The filter is placed in the fluid path of the insulin formulation. The distal end of the filter is surrounded with a porous cellulose acetate membrane for the purpose of preventing the Sephadex gel from entering the fluid path and being delivered to the patient. The pore diameter of the cellulose acetate is 0.22 µm. Before adding the insulin formulation to the filter, the filter beads are ideally exposed to an aqueous buffer such as phosphate buffer in order to swell the beads.

We claim:

1. A device for delivery of an insulin or insulin analog formulation and measurement of subcutaneous glucose concentration, comprising:
   a hollow tube comprising an inner lumen, an outer wall, a proximal end, and a distal end, wherein the proximal end is in fluid communication with a source of the insulin or insulin analog formulation, wherein the distal end is configured to deliver the insulin or insulin analog formulation subcutaneously, wherein the insulin or insulin analog formulation comprises an excipient comprising a phenol or cresol; and
   an amperometric glucose sensor disposed on the outer wall at a location no more than 7 millimeters (mm) away from the distal end, wherein the amperometric glucose sensor comprises:
   an electrode layer comprising at least one indicating electrode, wherein the electrode layer underlies a redox-catalytic layer comprising (1) an osmium-based redox mediator comprising an osmium compound covalently bound to a pyridine-based or imidazole-based ligand, and (2) an enzyme comprising glucose oxidase or glucose dehydrogenase,
   wherein the osmium-based redox mediator and the enzyme allow electron transfer from subcutaneous glucose to the at least one indicating electrode sufficient to cause a response of the amperometric glucose sensor to a subcutaneous glucose concentration at an applied bias potential of no more than +250 millivolts (mV) relative to a reference electrode, and
   wherein the applied bias potential of no more than +250 mV relative to the reference electrode allows the electrode layer to undergo substantially no electropolymerization of the excipient during continuous operation of at least one hour of the amperometric glucose sensor, thereby maintaining a sensitivity of the amperometric glucose sensor to the subcutaneous glucose concentration in presence of the insulin or insulin analog formulation.

2. The device of claim 1, wherein the at least one indicating electrode comprises gold, carbon, graphite, platinum, or iridium.

3. The device of claim 1, wherein the ligand is 4,4'-dimethyl-2,2'-bipyridine.

4. The device of claim 1, wherein the osmium-based redox mediator is bound to poly (4-vinyl pyridine) or poly (1-vinyl imidazole).

5. The device of claim 1, wherein the amperometric sensor further comprises a reference electrode disposed on the outer wall.

6. The device of claim 1, wherein the reference electrode comprises a silver/silver chloride (Ag/AgCl) reference electrode.

7. The device of claim 1, wherein the amperometric sensor further comprises an insulating layer and a metal layer, wherein the insulating layer and the metal layer are disposed on the outer wall, wherein the insulating layer is coupled to the metal layer, and wherein the metal layer is coupled to the electrode layer.

8. The device of claim 7, wherein the insulating layer comprises a polyimide or liquid crystal polymer.

9. The device of claim 7, wherein the metal layer has a thickness of at least 2 micrometers (µm).

10. The device of claim 7, wherein the metal layer comprises titanium, gold, or platinum.

11. The device of claim 7, wherein the electrode layer comprises a film having a thickness of less than 500 nanometers (nm).

* * * * *